United States Patent [19]
Barbee et al.

[11] Patent Number: 5,489,361
[45] Date of Patent: Feb. 6, 1996

[54] MEASURING FILM ETCHING UNIFORMITY DURING A CHEMICAL ETCHING PROCESS

[75] Inventors: Steven G. Barbee, Dover Plains; Tony F. Heinz, Chappaqua, both of N.Y.; Yiping Hsiao, San Jose, Calif.; Leping Li, Poughkeepsie; Eugene H. Ratzlaff, Hopewell Junction, both of N.Y.; Justin W. Wong, South Burlington, Vt.

[73] Assignee: International Business Machines Corporation, Armonk, N.Y.

[21] Appl. No.: 354,567

[22] Filed: Dec. 13, 1994

Related U.S. Application Data

[62] Division of Ser. No. 269,861, Jun. 30, 1994.

[51] Int. Cl.$^6$ ................................................. H01L 21/00
[52] U.S. Cl. ........................................ 156/627.1; 216/84
[58] Field of Search ................................. 156/626, 627, 156/657, 662, 345, 626.1, 627.1, 657.1, 662.1; 204/129.2; 216/84

[56] References Cited

U.S. PATENT DOCUMENTS

| | | | |
|---|---|---|---|
| 2,933,675 | 4/1960 | Hoelzle | 324/30 |
| 3,163,568 | 2/1961 | Mieux | 156/627 |
| 3,553,052 | 1/1971 | Jubb, Jr. | 156/345 |
| 3,874,959 | 4/1975 | Hoekstra | 156/7 |
| 3,959,046 | 5/1976 | Bussmann et al. | 156/7 |
| 3,964,956 | 6/1976 | Snyder | 156/345 |
| 4,220,508 | 9/1980 | Kotani et al. | 204/129.65 |
| 4,338,157 | 7/1982 | Kanda | 156/627 |
| 4,497,699 | 2/1985 | de Wit et al. | 204/129.2 |
| 4,621,037 | 11/1986 | Kanda et al. | 430/30 |
| 4,755,442 | 7/1988 | Hasebe et all. | 156/627 |
| 4,793,895 | 12/1988 | Kaanta et al. | 156/627 |
| 4,969,973 | 11/1990 | Rinck et al. | 156/627 |
| 4,989,157 | 1/1991 | Balisky | 156/345 X |
| 4,995,939 | 2/1991 | Ferenczi et al. | 156/627 |
| 5,071,508 | 12/1991 | Scheithauer | 156/627 |
| 5,081,421 | 1/1992 | Miller et al. | 324/671 |
| 5,198,072 | 3/1993 | Gabriel et al. | 156/627 |
| 5,338,390 | 8/1994 | Barbee et al. | 156/627 |

FOREIGN PATENT DOCUMENTS

| | | | |
|---|---|---|---|
| 55-46568 | 4/1980 | Japan | H01L 21/88 |
| 59-52838 | 3/1984 | Japan | 156/627 |
| 59-113626 | 6/1984 | Japan | 156/627 |
| 273634 | 3/1990 | Japan | 156/627 |
| 496346 | 3/1992 | Japan . | |
| 8100646 | 3/1981 | WIPO | 156/62 |

OTHER PUBLICATIONS

Goubau, W. M., "Capacitive Etch Rate Monitor for Dielectric Etching", IBM Technical Disc. Bulletin vol. 31, No. 1, Jun. 1988, 448–449.

Liu et al., "Resistance/Capacitance Methods for Determining Oxide Etch End Point", IBM Technical Disc. Bulletin vol. 16, No. 8, Jan. 1974, 2706–2707.

Hoekstra, J. P., "Establishing End Point During Delineation Process", IBM Technical Disc. Bulletin vol. 16, No. 6, Nov. 1973, 1717–1720.

Bassous et al., "An In-Situ Etch Rate Monitor Controller", IBM Technical Disc. Bulletin vol. 20, No. 3, Aug. 1977, 1232–1234.

Primary Examiner—William Powell
Attorney, Agent, or Firm—Dale M. Crockatt

[57] ABSTRACT

A contactless method and apparatus for real-time in-situ monitoring of a chemical etching process during etching of at least one wafer in a wet chemical etchant bath are disclosed. The method comprises the steps of providing two conductive electrodes in the wet chemical bath, wherein the two electrodes are proximate to but not in contact with a wafer; monitoring an electrical characteristic between the two electrodes as a function of time in the etchant bath of the at least one wafer, wherein a prescribed change in the electrical characteristic is indicative of a prescribed condition of the etching process; detecting a minimum and maximum value of the electrical characteristic during etching; determining the times of the minimum and maximum values; and comparing the times of the minimum and maximum values to determine a film etching uniformity value. Such a method and the apparatus therefor are particularly useful in a wet chemical etch station, and are useful for film deposition process quality control.

5 Claims, 1 Drawing Sheet

MEASURING FILM ETCHING UNIFORMITY DURING A CHEMICAL ETCHING PROCESS

The application is a division of application Ser. No. 08/269,861, filed Jun. 30, 1994.

BACKGROUND OF THE INVENTION

1. Field of the Invention

The present invention generally relates to a method and apparatus for monitoring the etching condition of a chemical etching process, and more particularly, to an improved contactless real-time in-situ method and apparatus for the same.

2. Discussion of the Related Art

Etching rates and etch end points must be carefully monitored and controlled in order to end etching processes at the desired time. In semiconductor processing, inadequate or excess etching time can result in undesirable film patterning. For instance, for semiconductor devices having film layers or features in the micron and sub-micron range, an inadequate etch or an excess etch would result in the insufficient removal or the excess removal of a desired layer. Insufficient removal of a desired layer can result in an undesired electrical open or electrical short when the desired layer to be removed is an insulator or a conductor, respectively. Additionally, if the etch is in excess, undercutting or punch through can occur resulting in poorly defined film patterning or total lift-off. Inadequate or excess etching time further leads to undesirable reliability problems in the subsequently fabricated semiconductor device. As a semiconductor wafer is extremely expensive due to many processing steps involved in the making thereof, the need to critically control the etching end point in an etching process is highly desirable.

An etch end point must be accurately predicted and/or detected to terminate etching abruptly. Etch rates, etch times, and etch end points are difficult to consistently predict due to lot-to-lot variations in film thickness and constitution, as well as etch bath temperature, flow, and concentration variability. That is, an etch rate is dependent upon a number of factors, which include, etchant concentration, etchant temperature, film thickness, and the film characteristics. Precise control of any of these factors can be very expensive to implement, for example, concentration control.

Film etching nonuniformity is decidedly disadvantageous in semiconductor processing. Where there is a spatially distributed film non-uniformity in a film to be etched, wafers must be overetched to completely etch the last-to-clear regions of the film. Thus there is necessarily a certain amount of overetching required. Non-uniformity can result from differences across the wafer in film thickness, or can result from differences in the physical or chemical properties of the film such as stoichiometry, density, or intrinsic stress. However, substantial overetching can lead to wafer yield loss and the decreased reliability of the resulting electronic devices. In addition, circuit dimensions must be made larger to allow for overetch tolerances. Therefore, uniform films are highly desirable in the manufacture of semiconductor devices. The optimal development environment for designing processes and processing tools that produce uniform films would have a quick, inexpensive, facile and accurate means of measuring total film uniformity. During the optimization of film deposition or growth, it is highly desirable to have quick feedback on the influence of process variables on the uniformity of the resulting film.

Currently, most etch rate end point determination techniques depend on indirect measurement and estimation techniques. Some etch monitoring techniques have relied on external measurements of film thickness followed by etch rate estimation and an extrapolated etch end point prediction. However, etch rates may vary due to batch-to-batch differences in the chemical and physical characteristics of the film or the etchant. These extrapolation methods are inadequate. Interrupted measurement techniques are also imprecise where the etch rate is not linear, such as where an induction period occurs at the beginning of the etch.

Previous methods for measuring film etching uniformity include optical techniques such as ellipsometry, reflectance spectroscopy, and the prism coupler method, on blanket films on monitor wafers. Film thicknesses measured on monitor wafers and even fiducial sites on product wafers do not always correlate to the actual film thicknesses in the region of interest (e.g. in contact holes, on stacks of films, etc.) in the device. These measurements are spatially discrete. They can be time-consuming especially when "complete" mapping of the thickness nonuniformity is needed to determine the maximum and minimum points across the film. Furthermore, optical measurements require expensive equipment and specialized training for unambiguous interpretation of results. They usually assume refractive index dispersion relations and optical constants of underlying films and substrates, which may be invalid. In addition, these techniques have limitations in the thickness ranges for which they are applicable.

Other methods include similar optical measurements of fiducial regions or discrete test wafers. However, such methods are expensive as portions of the wafer are occupied by non-product fiducial areas or require additional test wafers. Such optical methods are also subject to uncertainty resulting from turbidity of the etch bath and other optical effects and uncertainty resulting from non uniform films. Finally, such optical methods are subject to imprecision in the resulting estimate of overetch when the number of measured sites is insufficient or when the sections are not representative of the whole.

Real-time, in-situ monitoring is preferred. Some in-situ techniques monitor the etch rate of a reference thin film. This may require additional preparation of a monitor wafer containing the reference thin film or a suitable reference may be unavailable. Still other techniques require physical contact of electrical leads with the wafer being etched and electrical isolation of those leads and associated areas of the wafer from the etchant. This presents problems associated with contamination, contact reliability and reproducibility, and the physical constraints which affect ease of use in manufacturing or automation. Yet other in-situ techniques monitor the etch rate of a fiducial region of the product wafer and require optical access to the wafer in the wet etch bath. Such methods are expensive as portions of the wafer are occupied by non-product fiducial areas. Such optical methods are also subject to uncertainty resulting from turbidity of the etch bath and other optical effects and uncertainty resulting from non uniform films.

It would thus be desirable to provide an improved method and apparatus which provides non-contact, real-time, in-situ monitoring of an etching condition of a wafer being etched.

SUMMARY OF THE INVENTION

An object of the present invention is to overcome the problems in the art discussed above.

Another object of the present invention is to provide an improved non-contact method of monitoring the etching condition of a wafer being etched.

Yet another object of the present invention is to provide an accurate real-time, in-situ method and apparatus for monitoring an etching condition of a wafer being etched.

Yet another object of the present invention is to provide an accurate real-time, in-situ method and apparatus for controlling a wafer etching process.

According to the present invention, a contactless method for real-time in-situ monitoring of a chemical etching process for the etching of at least one wafer in a wet chemical etchant bath comprises the steps of:

a) providing two conductive electrodes in the wet chemical bath, wherein said two electrodes are proximate to but not in contact with the at least one wafer;

b) monitoring an electrical characteristic between the two electrodes as a function of time in the etchant bath of the at least one wafer, wherein a prescribed change in the electrical characteristic is indicative of a prescribed condition of the etching process;

c) detecting a minimum value of said electrical characteristic during etching;

d) determining the time of the minimum value of said electrical characteristic;

e) detecting a maximum value of said electrical characteristic during etching;

f) determining the time of the maximum value of said electrical characteristic; and g) comparing time of said minimum value and the time of said maximum value and determining a film etching uniformity value therefrom.

In addition, according to the present invention, a contactless real-time in-situ chemical etch monitor for providing an indication of a prescribed condition of an etching process of at least one wafer to be etched in a wet chemical etchant bath comprises a means for accomplishing each of the aforesaid process steps.

BRIEF DESCRIPTION OF THE DRAWINGS

The foregoing and other teachings and advantages of the present invention will become more apparent upon a detailed description of the best mode for carrying out the invention as rendered below. In the description to follow, reference will be made to the accompanying drawings, in which.

DETAILED DESCRIPTION OF THE PREFERRED EMBODIMENTS

Copending U.S. patent application Ser. No. 07/985,413, filed Dec. 4, 1992, now U.S. Pat. No. 5,338,390, entitled "Contactless Real-Time In-Situ Monitoring of a Chemical Etching Process," assigned to the assignee of the present invention (attorney docket FI9-92-152), the disclosure of which is hereby incorporated by reference into the present application, describes a related method and apparatus for the contactless, real-time, in-situ monitoring of a chemical etching process during etching of a wafer in a wet chemical etchant bath, wherein the two conductive electrodes are proximate to but not in contact with the at least one wafer, and further wherein said two electrodes are positioned on opposite sides of the wafer. Six copending U.S. Patent Applications, filed on even date herewith, which are Ser. No. 08/269,864, entitled "MINIMIZING OVERETCH DURING A CHEMICAL ETCHING PROCESS;" Ser. No. 08/269,862, entitled "REAL TIME MEASUREMENT OF ETCH RATE DURING A CHEMICAL ETCHING PROCESS;" Ser. No. 08/269,863, entitled "CONTACTLESS REAL-TIME IN-SITU MONITORING OF A CHEMICAL ETCHING PROCESS;" Ser. No. 08/269,860, entitled "METHOD AND APPARATUS FOR CONTACTLESS REAL-TIME IN-SITU MONITORING OF A CHEMICAL ETCHING PROCESS;" Ser. No. 08/269,859, now U.S. Pat. No. 5,451,289, entitled "FIXTURE FOR IN-SITU NON-CONTACT MONITORING OF WET CHEMICAL ETCHING WITH PASSIVE WAFER RESTRAINT;" and Ser. No. 08/269,865, now U.S. Pat. No. 5,445,705, "METHOD AND APPARATUS FOR CONTACTLESS REAL-TIME IN-SITU MONITORING OF A CHEMICAL ETCHING PROCESS;" and which are assigned to the assignee of the present invention, describe improvements to the method and apparatus for contactless, real-time, in-situ monitoring of chemical etching disclosed in the Ser. No. 07/985,413 application. The disclosure of the aforesaid six copending applications is also hereby incorporated by reference into the present application.

Figure 1:
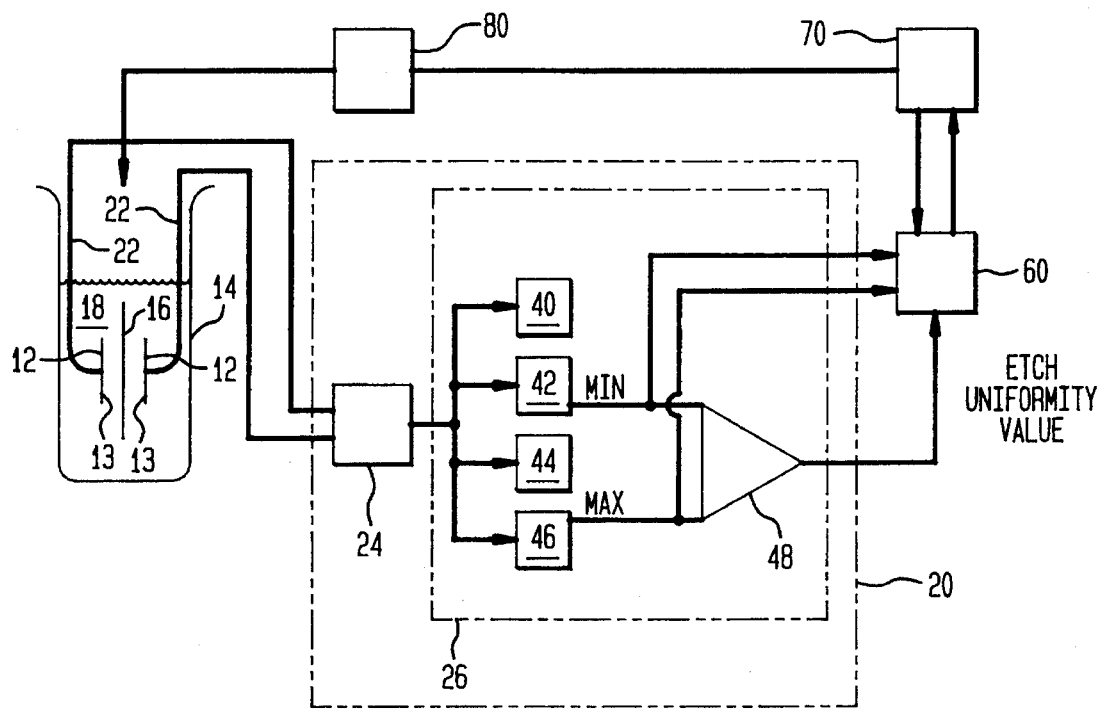
FIG. 1 shows a simplified block diagram of a contactless real-time in-situ etching condition monitor according to the present invention.

Referring now to FIG. 1, there is shown an improved contactless, real-time, in-situ monitor for providing an indication of a prescribed condition and determining an overetch value in an etching process according to the present invention. The monitor comprises at least two conductive electrodes 12 positionable inside an etchant tank 14. Etchant tank 14 is of an appropriate size for receiving at least one wafer 16 to be etched. The at least one wafer 16 comprises a semiconductor wafer having at least one film layer thereon which is desired to be removed by a chemical etchant bath 18. While only one wafer is shown, more than one wafer may be placed in the etchant bath 18.

Electrodes 12 are connected to an electrical characteristic monitoring device 20 by electrical wires 22. Electrical characteristic monitoring device 20 can comprise, for example, an impedance analyzer 24 and a data recording and analyzing device 26, such as a computer or a programmable controller. Monitoring of the prescribed etching characteristic is effected by electrically sensing, in-situ, changes in an electrical characteristic of the wafer, such as, the impedance or an element or elements of impedance (e.g., admittance, capacitance, inductance, reactance and/or resistance), between the two electrodes 12. For example, the real and imaginary parts of the impedance as a function of time may be measured. The output from analyzer 24 is an electrical signal which is proportional to a condition of the film to be etched and is a function of time.

Figure 2:
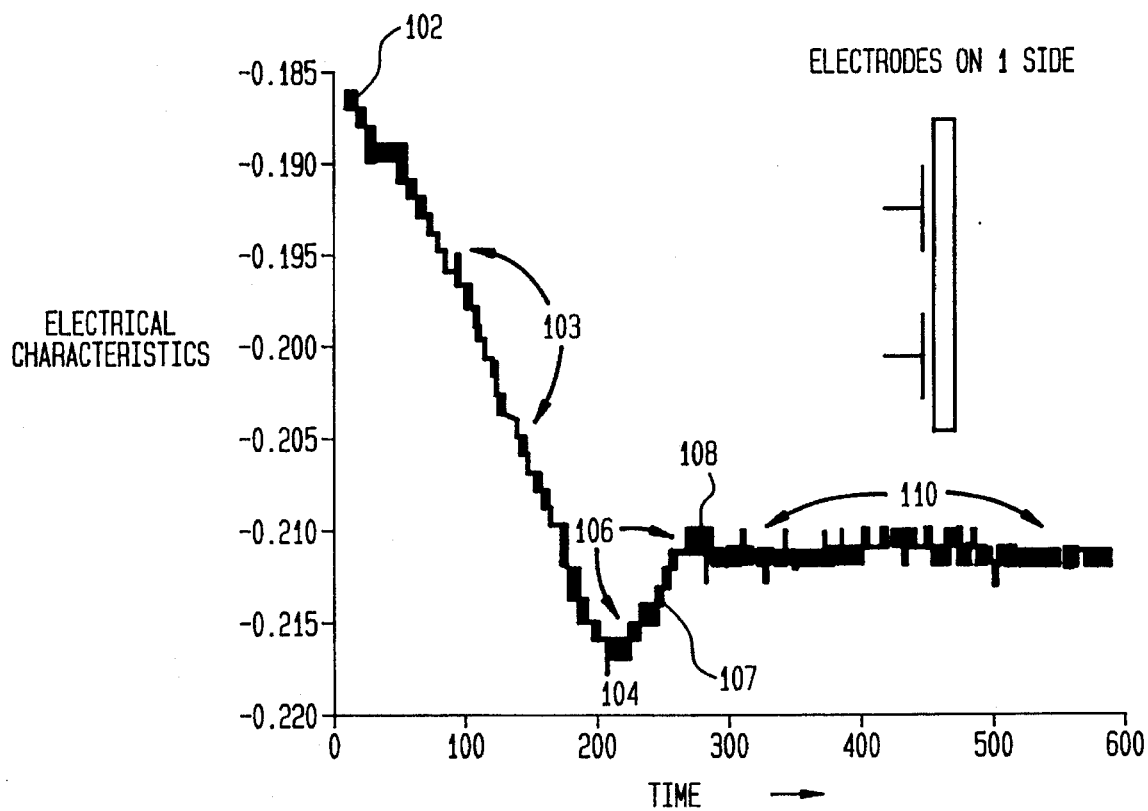
FIG. 2 shows a graph of monitored electrical characteristics according to the present invention.

In FIG. 2 there is shown a graphical representation as a function of time of a typical output signal from the electrical characteristic analyzer such as an impedance analyzer 24 described above. More particularly, FIG. 2, represents measured capacitance as a function of etch time, as disclosed in copending application U.S. patent application Ser. No. 07/985,413. Starting point 102 corresponds to the start of the etching process. Region 103 of the curve corresponds to thinning of the film during the etch process. Minimum point 104 corresponds to the point in time at which a first penetration of the film by the action of the etchant occurs. It will be understood that such first penetration or etch through or "opening" relates to a small portion of the overall area of the film. Region 106 of the curve corresponds to the period during which an increasing proportion of the film is etched away, that is, as the proportion of the etched area or "open" area becomes larger. Inflection point 107 has been found in this invention to correspond to a point in time at which a last etch through occurs, that is, the last feature to open has been penetrated, but not fully cleared, and at which time a "foot" usually remains. By "foot" is meant a last portion of material to be removed which remains within the partially open feature until the nominal feature size has been etched; in cross section a foot will usually be observed to extend into the open feature from the lower portion of the feature sidewall. Maximum point 108 corresponds to a point in time at which all features are etched to nominal size in an essentially uniform film. Region 110 of the curve corresponds to the period during which more than the nominal or desired amount of material to be removed by etching is being removed from the substrate, for example, by an undercutting process.

The time period between minimum point 104 and inflection point 107 in the curve of FIG. 2 represents the extent of nonuniformity in the film thickness for the case where the film is homogeneous, that is, has a linear etch rate per unit of thickness at all points on the wafer. The shorter the time duration, the more uniform the film thickness is. The contrary also holds true. Based on the time duration between these points, the extent of uniformity of the film can be immediately discerned. Alternatively, where thickness can be shown to be extremely uniform, the nonuniformity may be attributed to other physical or chemical phenomena. This information is not from a series of discrete measurements across the film, as in optical approaches, but is from a single measurement representative of the whole wafer. In one measurement, the relative difference between the absolute maximum and absolute minimum thickness is obtained. In deposition process development, the goal is to maximize the corresponding slope on the characteristic curve obtained by the wet etch monitor system.

Returning to FIG. 1, the data recording and analyzing device 26 receives the output signal from the analyzer 24. Data recording and analyzing device 26 comprises well known elements of (a) means 40 for detecting a minimum value of the electrical signal as a function of time; (b) means 44 for detecting a maximum value of the electrical signal as a function of time; (c) means 42 for determining the time of the minimum value; (d) means 46 for determining the time of the maximum value; (e) means 48 for comparing time of said minimum value and the time of said maximum value and determining a film etching uniformity value therefrom. It will be apparent that the means for detecting either a maximum or a minimum or both may be combined with the means for determining the respective time or times thereof.

As further shown by FIG. 1, an alternative embodiment of the present invention may include a means 60 for determining an etching end point, which means is responsive to any one or more of the time of the minimum value, the time of the maximum value, the time of the inflection point 107, and the etching uniformity value. Means 60 for determining an etching end point may be separate from, or part of, electrical characteristic monitoring device 20.

In yet another alternative embodiment, the apparatus of the present invention may comprise a means 70 such as a computer or a programmable controller which is responsive to the end point determined by means 60, and which means 70 may, in turn, control the etch process such as by actuating a wafer handling means 80. Furthermore, electrical characteristic monitoring device 20 can likewise comprise an impedance analyzer and a computer or a programmable controller, the computer or programmable controller providing feedback control to initiate, control, and terminate an etching operation. Impedance analyzers, computers, and programmable controllers are well known in the art.

Not shown, but contemplated as an alternative embodiment within the scope of the present invention, is a method and apparatus which detects and is responsive to inflection point 107 in determining a film etching uniformity value and/or end point. For example, the practitioner will understand that the maximum point may be anticipated from the detected minimum point and the inflection point, and the film etching uniformity determined therefrom in order to minimize overshooting the etching end point.

Finally, it is noted that many of the disclosed means may be assembled as discrete elements or together in a combined element without affecting the essential function thereof.

It should be understood that the invention contemplates that the shape of the curve shown in FIG. 2 may deviate from that shown in the figure, provided however, that a maximum point and a minimum point must be detected, or alternatively, at least one of a maximum point or a minimum point must be detected together with inflection point 107. The order of occurrence of minimum point 104 and maximum point 108 of the curve may be inverted, with the maximum occurring before the minimum. Furthermore, the in situ etch monitor may record the etch rate as a function of time. This results in an etch record which is essentially a monolayer-by-monolayer etch rate depth profile of the thin film strata. Any change in the ongoing etch rate is observed as a change in the curve shape. Thus, any significant batch-to-batch variation in the homogeneity of a film that would affect the etch rate will be reflected in the batch-to-batch reproducibility of the etch records. For example, a temporary or intermittent pressure or electrical fluctuation in a film deposition process could result in transient density or stoichiometry changes in the resulting film. Such changes would appear as small spikes or plateaus in the etch record. Batch-to-batch thin film thickness and uniformity reproducibility may be correlated and monitored by correlating and monitoring etch monitor results.

Thus there has been shown an improved real-time in-situ monitoring method and apparatus which provide accurate, non-contact, monitoring of an etching characteristic of an etching process. Such a method and apparatus are inexpensive to implement and ensure the integrity of the etched wafer or wafers. Etching of a wafer can be controlled precisely.

While the invention has been particularly shown and described with reference to specific embodiments thereof, it will be understood by those skilled in the art that various changes in form and detail may be made thereto, and that other embodiments of the present invention beyond embodiments specifically described herein may be made or practiced without departing from the spirit of the invention. System condition parameters, such as impedance analyzer frequency, etc., may need to be adjusted accordingly to obtain optimum detection sensitivity. Similarly, other changes, combinations and modifications of the presently disclosed embodiments will also become apparent. The embodiments disclosed and the details thereof are intended to teach the practice of the invention and are intended to be illustrative and not limiting. Accordingly, such apparent but undisclosed embodiments, changes, combinations, and modifications are considered to be within the spirit and scope of the present invention as limited solely by the appended claims.

What is claimed is:

1. A method for contactless, real-time, in-situ monitoring of a chemical etching process during etching of at least one wafer in a wet chemical etchant bath, said method comprising the steps of:

a) providing two conductive electrodes in the wet chemical bath, wherein said two electrodes are proximate to but not in contact with the at least one wafer;

b) monitoring an electrical characteristic between the two electrodes as a function of time in the etchant bath of the at least one wafer, wherein a change in the electrical characteristic is indicative of a state of the etching process;

c) detecting a minimum value of said electrical characteristic during etching;

d) determining a time of the minimum value of said electrical characteristic;

e) detecting a maximum value of said electrical characteristic during etching;

f) determining a time of the maximum value of said electrical characteristic; and g) comparing the time of said minimum value and the time of said maximum value and determining a film etching uniformity value therefrom.

2. The method of claim 1, wherein the monitoring of an electrical characteristic in step (b) comprises monitoring impedance and further wherein the change in the electrical characteristic comprises a change in impedance.

3. The method of claim 2, wherein the monitoring of an electrical characteristic in step (b) comprises monitoring impedance and further wherein the change in the electrical characteristic comprises a change in a component of impedance, wherein said component is selected from the group consisting of admittance, reactance, resistance, capacitance, and inductance.

4. The method of claim 1, wherein an etching end point is determined in real time in response to said film etching uniformity value and an etching starting point.

5. The method of claim 4, further comprising the step of controlling the etching process in response to the etching end point, wherein the end point is determined in real time.

* * * * *